United States Patent [19]

Lecomte

[11] Patent Number: 4,843,245

[45] Date of Patent: Jun. 27, 1989

[54] SCINTILLATION DETECTOR FOR TOMOGRAPHS

[75] Inventor: Roger Lecomte, Sherbrooke, Canada

[73] Assignee: Universite de Sherbrooke, Sherbrooke, Canada

[21] Appl. No.: 58,363

[22] Filed: Jun. 4, 1987

[30] Foreign Application Priority Data

Jun. 6, 1986 [CA] Canada ................................. 510983

[51] Int. Cl.⁴ ...................... G01T 1/164; G01T 1/202
[52] U.S. Cl. ................................ 250/367; 250/363.04
[58] Field of Search .......... 250/367, 363 SR, 363 SA, 250/363 SB, 363 SE

[56] References Cited

U.S. PATENT DOCUMENTS

| | | | |
|---|---|---|---|
| 2,910,592 | 10/1959 | Armistead | 250/367 |
| 3,851,177 | 11/1974 | Van Dijk et al. | 250/366 |
| 3,899,675 | 8/1975 | Floyd | 250/366 |
| 3,919,556 | 11/1975 | Berninger | 250/366 |
| 3,955,088 | 5/1976 | Muehllehner | 250/369 |
| 4,037,105 | 7/1977 | Laurer | 250/367 |
| 4,075,483 | 2/1978 | Tancrell et al. | 250/366 |
| 4,095,107 | 6/1978 | Genna et al. | 250/363 S |
| 4,124,804 | 11/1978 | Mirell | 250/363 S |
| 4,323,778 | 4/1982 | Wykes et al. | 250/367 |
| 4,398,092 | 8/1983 | Carlson | 250/363 R |
| 4,675,526 | 6/1987 | Rogers et al. | 250/263 SR |
| 4,677,299 | 6/1987 | Wong | 250/367 |

OTHER PUBLICATIONS

Entine et al., "Scintillation Detectors Using Large Area Silicon Avalanche Photodiodes", *IEEE Transactions on Nuclear Science*, vol. NS-30, No. 1, Feb. 1983, pp. 431-435.

"A High Resolution Positron Camera", L. Eriksson, C. Bohm, M. Kesselberg, J. E. Litton, M. Bergstrom, and G. Blomqvist, pp. 33-45.

Primary Examiner—Janice A. Howell
Assistant Examiner—William F. Rauchholz
Attorney, Agent, or Firm—Cushman, Darby & Cushman

[57] ABSTRACT

The present invention relates to a scintillation detector for a tomograph comprising at least two scintillators having different scintillation characteristics and being optically coupled to a photodetector.

7 Claims, 4 Drawing Sheets

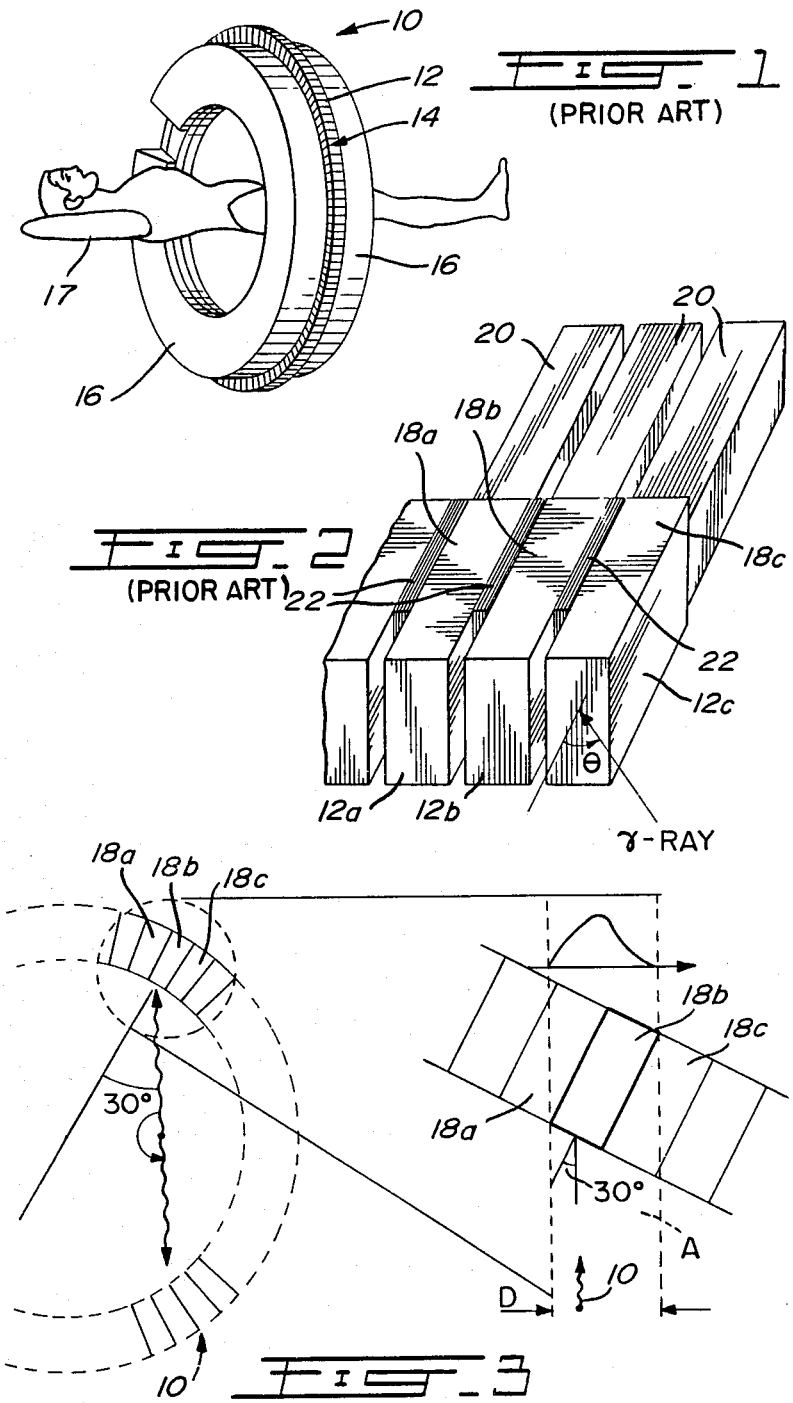

SCINTILLATION DETECTOR FOR TOMOGRAPHS

FIELD OF THE INVENTION

The present invention relates to a novel scintillation detector for a tomograph. By extent the invention also comprehends a detector array and a tomograph using such a scintillation detector.

BACKGROUND OF THE INVENTION

Nuclear medicine uses radiopharmaceutical products marked by radioactive isotopes emitting gamma radiation for obtaining information on the physiological processes of the human body. The progression of the radioactive products toward an organ or its accumulation in that organ are followed from outside the body by means of a gamma radiation detector, more or less sophisticated, the most common being the scintillation camera or gamma camera of the Anger type. The image obtained by such a camera represents the projection on a reference plane of the three dimensional distribution of the radiopharmaceutical product. A three dimensional image may be obtained by applying the well-known principles of the axial tomography.

Another approach, perhaps less popular but offering many advantages, uses as tracers atoms emitting positrons. The positrons annihilate themselves with electrons and generate two gammas of 511 keV emitted at 180° relatively to each other. By detecting coincidentally these two gammas with two diametrically opposite detectors, the trajectory on which the disintegration has occurred may be determined. By superposing, by means of known techniques of tomographic reconstruction, the multiple trajectories measured by an array of detectors surrounding the source, the distribution of the radioactivity in the volume enclosed by the array of detectors may be derived. The three dimensional image may be obtained by the juxtaposition of two-dimensional images of the radioactivity distribution in adjacent planes, or by direct reconstruction from the multiple inter-plane trajectories.

A typical tomograph comprises an array of individual detectors either separated or not separated, by septa. The detectors may be grouped in the array into one or more rings. The array surrounds the body to be scanned and a suitable electronic circuitry processes the electric signals generated by the detectors so as to obtain the desired image. Typically, the diameter of a detector ring varies from 50 to 100 cm, according to whether the apparatus is adapted for scanning the brain or the entire body. The majority of the existing cameras use ($Bi_4Ge_3O_{12}$) scintillation detectors (hereinafter "BGO") coupled to photomultiplier tubes. Such cameras have a spatial resolution in the order of one centimeter. Certain models can reach a resolution of 4 to 6 mm FWHM. These resolution values are not the inherent theoretical limits fixed by the position range in tissues and the non-colinearity of emission of annihilation gamma-rays, but rather represent a compromise resulting from physical and technological restrains.

The improvement of the resolution of a tomograph up to three millimeters FWHM, which is close to the theoretical limit, is highly desirable. However, the parallax error which exists in a detector ring has, up to now prevented such improvement out of the region very close to the center of the tomograph.

The parallax error may briefly be defined as the lack of information on the radial position of interaction of a gamma ray in a given detector of the ring. The position of interaction in a detector is a function of probability. In some cases, a gamma ray may pass through a detector without interacting therein and interact in an adjacent detector. Therefore, when a detector generates an output signal, indicating the occurrence of an interaction, the gamma ray may come from anywhere within the channel defined by the projection of the volume of the detector, with a distribution given by the probability of interaction of the gamma in this detector (the so-called "aperture function").

At first sight, a simple way to resolve the parallax problem is to reduce the depth of the detectors to lower the volume of the projection channel to, in turn, reduce the incertitude region and the parallax error. However, a thinner detector implies that more gamma rays will pass throughout without interacting, resulting in a loss of efficiency which may not be acceptable for clinical applications. In a similar manner, the increase of the ring diameter will reduce the parallax error, involving a reduction of efficiency of the device and an increase of the costs due to the larger number of detectors necessary to construct a bigger ring.

An alternative solution which has been adopted in several of the commercially available tomographs consists of inserting septa of a heavy metal (Tungsten, Gold or Uranium) between the detectors to reduce the possibility of a gamma ray passing from one detector into another. To efficiently stop a gamma ray of 511 keV, the septa must be sufficiently thick (more than one mm). However, in a high resolution system where the detectors are typically 3 or 4 millimeters thick, the drop of efficiency of 25 to 50% which would results from the use of such septa, is obviously undesirable.

OBJECTS AND STATEMENT OF THE INVENTION

An object of the present invention is a scintillation detector for a tomograph, the detector having an increased resolution.

Another object of the invention is an array of scintillation detectors for a tomograph, the array having an increased resolution.

A further object of this invention is a tomograph with an improved resolution.

The objects of this invention are achieved by providing a scintillation detector sensible to the position of interaction of a gamma ray therein. In other words, the position of interaction of the gamma ray in the detector may be determined with a certain precision, for reducing the parallax error.

In one embodiment, the detector comprises two scintillators having different scintillation characteristics and optically coupled to each other. To one of the scintillators is connected a photodetector which generates an electrical signal in response to a flash of light produced by one of the scintillators due to an interaction of a gamma ray. Since the scintillators have different scintillation characteristics, different signals will be generated by the photodetector depending whether the gamma has interacted in the first or the second scintillator. By using known signal discrimination techniques, the scintillator in which the interaction has occurred, may be determined.

For further increasing the resolution, the detector may be formed of more than two scintillators.

It should be understood that the term "light" includes not only visible light but also other types of electromagnetic radiation such as ultraviolet light or others.

The concept behind the scintillation detector of this invention is not restricted only to the detection of gamma radiation. When other types of radiation are to be detected, appropriate scintillators responsive to the emitted radiation must be used for the construction of the detector.

Such variations of this invention are well within the reach and the knowledge of a person skilled in the art and for that reason they will not be explored in detail here.

A plurality of detectors according to this invention are mounted together, and grouped together, preferably in one-dimensional or two-dimensional arrays. In a tomograph, each detector is formed by a plurality of scintillators and a photodetector, the photodetectors being mounted at the periphery of the ring. When a plurality of rings are used, they are mounted side by side so as to obtain images in a plurality of adjacent planes. Alternatively, two-dimensional arrays of detectors can be used, each detector being formed by a plurality of scintillators with the photodetectors mounted on top of the array. The tomograph has the form of a cylindrical array of detectors.

Preferably, the scintillation detectors are optically isolated from each other in the array.

A tomograph according to this invention typically includes an array of scintillation detectors to which is connected a signal processing system, for analyzing the electric signals generated by the photo-detector so as to construct an image on a monitor or a representation in any other form of the organ or the body which is scanned.

The present invention comprises in a most general aspect a tomograph for obtaining information on a human body or an animal emitting radiation, the tomograph comprising:

radiation detecting means comprising an array of radiation detectors optically isolated from each other, each detector including:
(a) a scintillator having a multi-layered structure, each layer having a unique scintillation timing constant in the detector, the layers of the detector being arranged one on top of the other in a path of travel of radiation from the human body or animal toward the radiation detecting means, the scintillator defining a light guide;
(b) a photo-detector optically coupled to the lightguide, the photo-detector generating an electric signal in radiation interacting therein, the electric signal being representative of the scintillation timing constant of the layer of the scintillator in which an interaction has occurred;
processing means operatively connected to the photo-detectors of the radiation detectors of the array for processing the signals generated by the photo-detectors to provide the information, the processing means comprising signal discrimination means to identify the layer of a scintillator of a radiation detector in which an interaction has occurred.

BRIEF DESCRIPTION OF THE DRAWINGS

FIG. 1, is a perspective view of a prior art array of scintillation detectors forming a ring;

FIG. 2, is an enlarged perspective view of a portion of the array shown in FIG. 1;

FIG. 3, is a schematical view of a detector ring, illustrating the parallax error phenomena;

FIG. 4a is a diagram of the signals generated by a photodetector in response to an interaction of a gamma ray in three different scintillators. It shows the difference in decay time of the scintillation light in each of the scintillators. FIG. 4b is the diagram of the corresponding signals at the output of an integrating amplifier;

DESCRIPTION OF A PRIOR ART DEVICE

Figure 4:
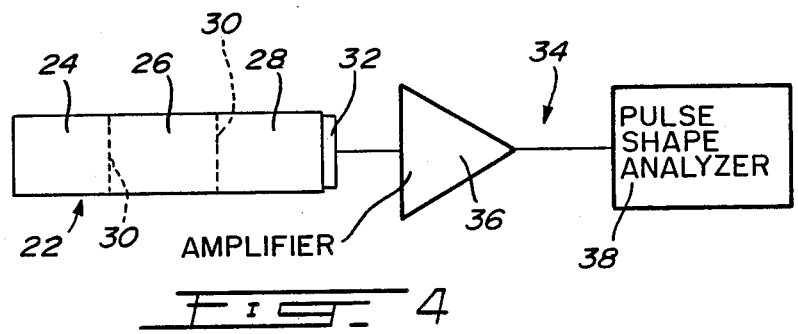
FIG. 4, is a schematical view of a scintillation detector according to the present invention coupled to a signal discrimination circuit.

A typical detector array 10 for a tomograph is illustrated in FIG. 1. Array 10 is constituted by a plurality of individual scintillation detectors 12 grouped in a ring 14. Ring 14 is sandwiched between two conventional lead shielding rings 16.

Detector ring 10 is of a size to accomodate a human body 17 which has previously been injected with a substance producing an emission of gamma rays in opposite directions, at 180° from each other. The gamma rays are coincidently detected by two opposed scintillation detectors 12 to determine the trajectory of the gamma rays.

Suitable electronic detection and processing circuitry is used to construct an image of the organ in which the radioactive substance is accumulated, in the plane of the detector ring 14, from the signals generated by the detectors of array 10.

Referring to FIG. 2, illustrating a group of three adjacent scintillation detectors 12a, 12b and 12c, the detectors comprising scintillators 18a, 18b and 18c, respectively, known in the art. When a gamma ray passes through scintillator 18b, it interacts therein and produces a flash of light detected by a photodetector 20 (usually a photomultiplier tube), mounted on top of scintillator 18b. Tungsten septa 22 may be inserted between the detectors so as to prevent the passage of gamma rays from one detector to another.

Referring to FIG. 3, when gamma rays are emitted from the human body 17, near the periphery of the detector ring 14, they penetrate the scintillator 18b at an incident angle which increases as the point of emission of the gamma rays is near the periphery of ring 14. In the example given in FIG. 3, the incident angle is of 30°, but the following also holds true for other values of incident angles.

When a gamma ray penetrates scintillator 18b the position of interaction in the scintillator is a function of probability. In extreme cases, the gamma ray may pass through scintillator 18b without interacting, penetrate crystal 18a, in the absence of Tungsten septa, and interact in scintillator 18a. Similarly, a gamma ray may pass through scintillator 18c and interact in scintillator 18b. Therefore, when a detector generates an output signal, a gamma ray which has interacted therein, may have been emitted anywhere within the zone identified by the reference letter A. Zone A has a width D which corresponds to the uncertainty on the position of the source for an incidence angles of 30°. This incertitude which has previously been defined as the parallax error, is obviously undesirable and increases as the position of emission of the gamma ray is near the periphery of ring 14.

DESCRIPTION OF THE PREFERRED EMBODIMENT

FIG. 4 illustrates schematically a detector 22 according to the present invention which comprises three scintillators 24, 26 and 28 respectively optically coupled to each other through optical contacts 30. Each scintillator has different scintillation characteristics. A photodetector 32 such as an avalanche photodiode is mounted to scintillator 28.

As an example, avalanche photodiodes manufactured by RCA and sold under the part number C30994E, may be used for the construction of scintillation detectors according to this invention.

The assembly of scintillators 24, 26 and 28 defines a light guide which transmits the flash of light generated in response to an interaction of a gamma ray, in any one of the scintillators to the photodetector 32.

Scintillation detector 22 is connected to an amplification and signal discrimination circuit 34 comprising an integrating amplifier 36 connected to photodetector 32. A pulse shape analyzer 38 is connected to amplifier 36.

Figure 4A:
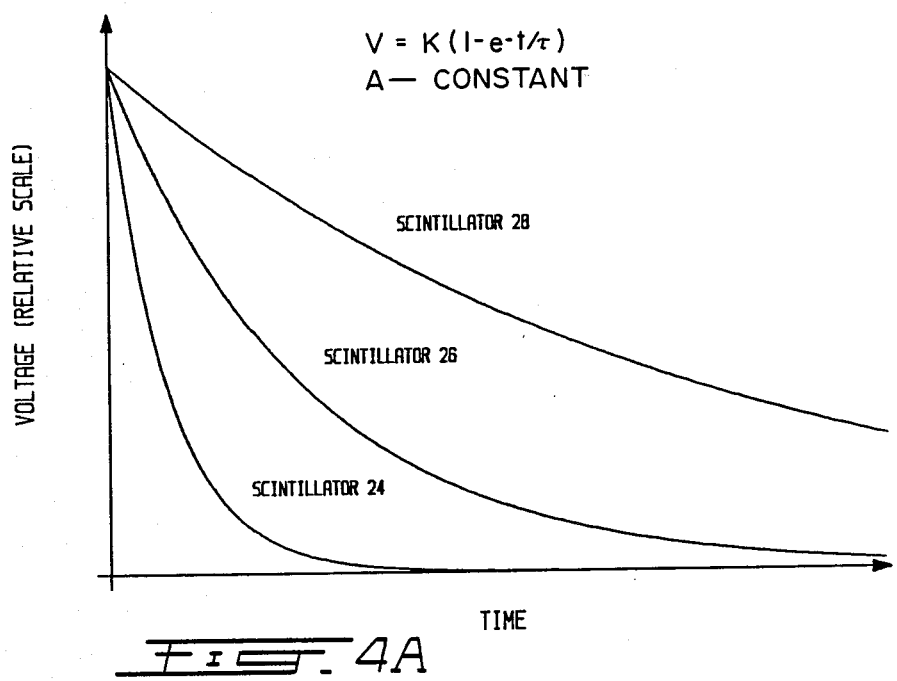
FIGS. 4a and 4b.
Figure 4B:
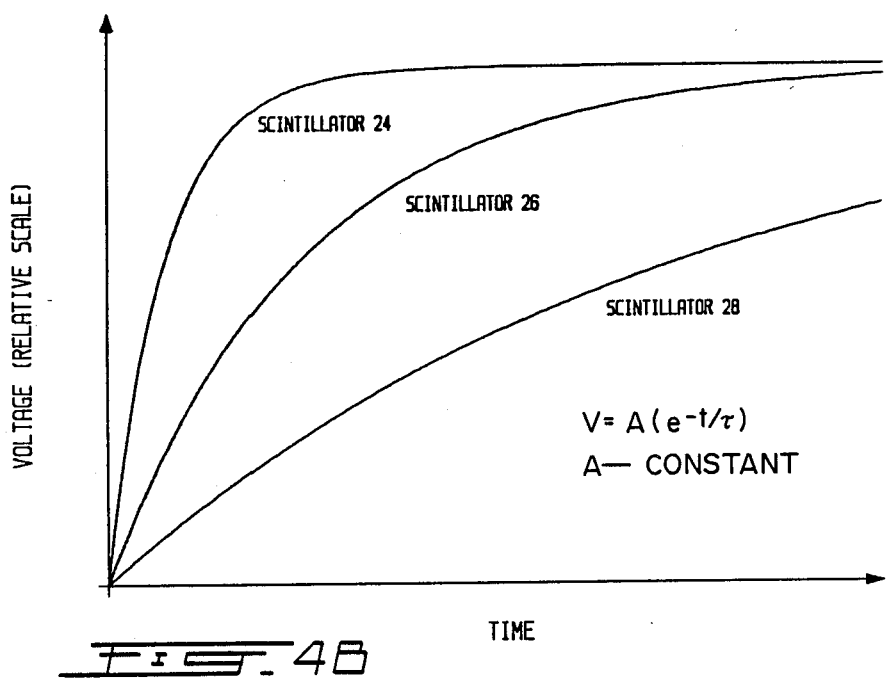

Since the scintillators 24, 26 and 28 have different scintillation characteristics, when a gamma ray interacts in detector 22, it suffices to observe the decay time of the output signal generated by photodetector 32 or the rise time of the integrated signal at the output of integrated amplifier 36 to determine in which scintillator the interaction has occured. FIGS. 4a and 4b are diagrams of the output signals from photodetector 32 and from integrating amplifier 36, respectively, produced in response to an interaction in each scintillator of detector 22. The decay and the rise times of the signals associated with each scintillator are different which allows to determine in which scintillator the gamma ray has interacted.

Electronic circuit 34 for discriminating signals having different rise or decay times is well known in the art and, for that reason, it will not be described in detail here.

By constructing each detector of a plurality of individual scintillators, results, for all practical purposes, in a reduction of the depth of the detector without a substantial reduction in the efficiency thereof.

Figure 5:
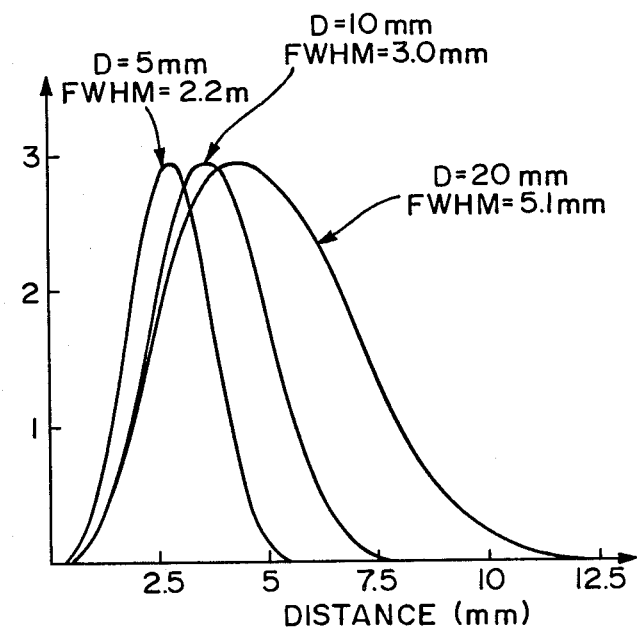
FIG. 5 is a diagram of aperture functions illustrating the resolution improvement obtained with the scintillation detector of this invention.

FIG. 5 shows the resolution improvement which may be obtained with the detector according to the present invention. It may be observed that, for a prior art detector formed by a single scintillator having a depth of 20 mm irradiated at an angle of 30°, the resolution is of 5.1 mm. However, when a detector according to the present invention, formed by 4 scintillator crystals having each a depth of 5 mm is used, the resolution is of 2.2 mm, a significant improvement. However, the overall depth of the detector is still 20 mm which implies that there is little or no drop in the efficiency.

A small loss of efficiency may be expected in the multiscintillator system according to this invention resulting from the use of scintillation crystals which have less ability to stop gamma rays than the BGO crystal being one of the most efficient. For example, with a two scintillator detector, BGO/GSO ($Gd_2SiO_5$), a drop of efficiency of about 5% may be expected, which is tolerable.

Figure 6:
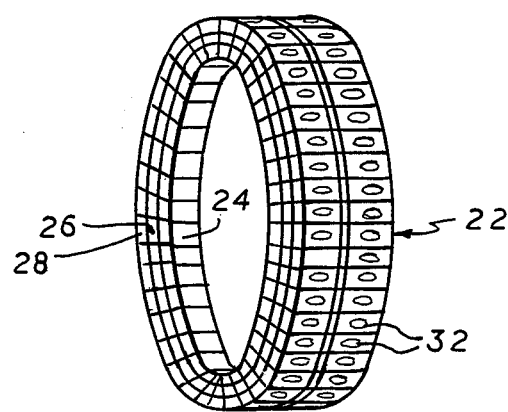
FIG. 6 is a schematic view of a two dimensional array of scintllation detectors, the detectors being arranged side by side along the same axis.

A plurality of scintillation detectors are mounted side by side without interacting optically with each other. This may be achieved by optically isolating the detectors from each other. The scintillation detectors from a one-dimensional or a two-dimensional array. In each detector of the array, the photodetector is mounted on one end of the scintillator assembly and aligned with the scintillators. The array may have the shape of a ring closely resembling the detector ring shown in FIG. 1, or any other shape surrounding the body to be examined, with the photodetectors extending on the periphery of the ring. With such an arrangement, a plurality of adjacent rings may be placed side by side along the same axis, such as the array shown in FIG. 6 to obtain at the same time images in a plurality of adjacent planes. Alternatively, a two dimensional array may have the shape of a cylinder or any other shape surrounding the body to be examined with the photodetectors extending on the periphery of the cylinder, therefore allowing the three-dimensional image of a complete volume to be obtained simultaneously.

A tomograph according to this invention comprises one or more detector rings, or a cylinder or any other shape surrounding the body to be examined, formed by a two-dimensional array of detectors, to which is connected a signal processing and analysis circuitry, generally known in the art. This circuitry permits to analyze the signals generated by the photodetectors so as to construct an image on a monitor or in any other form of the specimen under observation.

It should be understood that the scope of the present invention is not intended to be limited to the specific preferred embodiment illustrated in the drawings and described above.

I claim:

1. A tomograph for obtaining information on a subject emitting radiation, said tomograph comprising:
    radiation detecting means comprising an array of radiation detectors which are optically isolated from each other each said detector including:
    (a) a scintillator having a multi-layered structure, each layer having a scintillation timing constant which is different from all other timing constants of other layers in the detector, the layers of the detector being arranged one on top of the other in a direction of the path of travel of radiation from said subject toward said radiation detecting means, said multi-layered scintillator defining a light guide; and
    (b) a photodetector optically coupled to said light-guide, said photodetector generating an electric signal indicative of a scintillation in said scintillator caused by radiation interacting therewith, said electric signal being representative of the scintillation timing constant of the layer of said scintillator in which an interaction has occurred; and
    processing means, operatively connected to the photodetectors of the radiation detectors of said array, for processing the signals generated by said photodetectors to provide said information, said processing means comprising signal discrimination means for identifying a particular layer of a scintillator of a radiation detector in which an interaction has occurred.

2. A tomograph as defined in claim 1, wherein said radiation is gamma radiation.

3. A tomograph as defined in claim 1, wherein each layer of the scintillator and the photodetector of the radiation detector are aligned along an axis.

4. A tomograph as defined in claim 1, wherein the radiation detectors of said array surrounds at least partially said subject emitting radiation.

5. A tomograph as defined in claim 1, wherein the radiation detectors of said array are grouped in plurality of adjacent axially aligned rings.

6. A tomograph as defined in claim 1, wherein the photodetectors are photodiodes.

7. A tomograph as defined in claim 6, wherein said photodiodes are avalanche photodiodes.

* * * * *